United States Patent [19]
Sheu et al.

[11] Patent Number: 5,414,145
[45] Date of Patent: May 9, 1995

[54] PRODUCTION OF TERTIARY BUTYL ALCOHOL FROM ISOBUTANE

[75] Inventors: Yu-Hwa E. Sheu, Hsinchu, Taiwan, Prov. of China; John R. Sanderson, Leander, Tex.; Mark A. Mueller, Austin, Tex.; William A. Smith, Houston, Tex.

[73] Assignee: Texaco Chemical Inc., White Plains, N.Y.

[21] Appl. No.: 288,842

[22] Filed: Aug. 11, 1994

[51] Int. Cl.$^6$ .............. C07C 29/132; C07C 31/12; C07C 41/01; C07C 301/19
[52] U.S. Cl. .................. 568/671; 549/529; 568/909.8; 568/910; 568/922
[58] Field of Search .......... 568/909.8, 910, 922, 568/671; 549/529

[56] References Cited

U.S. PATENT DOCUMENTS

| | | | |
|---|---|---|---|
| 4,810,809 | 3/1989 | Sanderson et al. | 549/529 |
| 4,992,566 | 2/1991 | Marquis et al. | 549/529 |
| 5,093,506 | 3/1992 | Marquis et al. | 549/529 |
| 5,151,530 | 9/1992 | Marquis et al. | 568/909.8 |
| 5,274,138 | 12/1991 | Keating et al. | 549/529 |

Primary Examiner—Joseph E. Evans
Attorney, Agent, or Firm—James L. Bailey; Kenneth R. Priem; Carl G. Ries

[57] ABSTRACT

Tertiary butyl alcohol (TBA) is prepared by non-catalytically reacting isobutane with oxygen to provide a reaction product comprising isobutane, peroxides including tertiary butyl hydroperoxide and impurities, charging the de-isobutanized reaction product and a soluble hydroperoxide decomposition catalyst to a first hydroperoxide decomposition reactor fitted with a fractionating column to provide a liquid reaction product comprising TBA, catalyst, hydroperoxides, and contaminants, and a vaporized decomposition product, cooling said vaporized reaction product to provide a condensate, and recovering a portion as a TBA reaction product, charging the liquid reaction product to a second hydroperoxide decomposition reactor to substantially completely decompose the peroxides therein and to form a second hydroperoxide decomposition product, which is charged to a second distillation column and separated therein into a third lighter overhead fraction comprising TBA, and a third heavier liquid fraction comprising normally liquid reaction byproducts, including TBA and residual quantities of hydroperoxide contaminants, recycling the third heavier fraction to the first hydroperoxide decomposition reactor and recovering TBA from the third lighter overhead fraction.

7 Claims, 2 Drawing Sheets

PRODUCTION OF TERTIARY BUTYL ALCOHOL FROM ISOBUTANE

BACKGROUND OF THE INVENTION

1. Field of the Invention

This invention relates to a plural stage process for the production of tertiary butyl alcohol from isobutane. More particularly, this invention relates to a plural stage process for the production of tertiary butyl alcohol from isobutane wherein isobutane is initially noncatalytically reacted with oxygen to prepare a reaction mixture comprising tertiary butyl alcohol and tertiary butyl hydroperoxide and wherein the tertiary butyl hydroperoxide is subsequently converted to an additional quantity of tertiary butyl alcohol. Thus, in accordance with the present invention, isobutane may be noncatalytically reacted with oxygen to provide an initial liquid reaction product comprising tertiary butyl hydroperoxide and tertiary butyl alcohol. All or a portion of the initial reaction product may be thereafter brought into contact with a soluble peroxide decomposition catalyst in a first decomposition zone in order to convert a portion of the tertiary butyl hydroperoxide to tertiary butyl alcohol and to provide a second liquid reaction product. The second liquid reaction product may be further treated in a second decomposition zone with a soluble hydroperoxide decomposition catalyst to decompose residual quantities of hydroperoxide in order to provide a substantially peroxides-free tertiary butyl alcohol product which may be used, for example, for reaction with methanol in a methyl tertiary butyl ether reaction zone to produce methyl tertiary butyl ether. A portion of the tertiary butyl hydroperoxide from the initial liquid reaction product may be used as a feedstock for an epoxidation reaction process for converting propylene and tertiary butyl hydroperoxide to propylene oxide and tertiary butyl alcohol.

2. Prior Art

It is known to noncatalytically react isobutane with oxygen in the liquid phase in order to provide a reaction product comprising a mixture of tertiary butyl hydroperoxide and tertiary butyl alcohol as illustrated, for example, by Winkler et al. U.S. Pat. No. 2,845,461.

It is known to react isobutane with oxygen in the presence of a soluble homogeneous peroxidation catalyst in order to provide a reaction product comprising tertiary butyl alcohol and residual tertiary butyl hydroperoxide as shown, for example, by Grane et al. U.S. Pat. No. 4,294,999, and Grane et al. U.S. Pat. No. 4,296,262.

It is known to prepare tertiary butyl alcohol by the catalyzed decomposition of tertiary butyl hydroperoxide as shown, for example, Sanderson et al. U.S. Pat. No. 4,912,266, Sanderson et al. U.S. Pat. No. 4,910,349, Sanderson et al. U.S. Pat. No. 4,912,267, Sanderson et al. U.S. Pat. No. 4,922,033, Sanderson et al. U.S. Pat. No. 4,922,034, Sanderson et al. U.S. Pat. No. 4,922,035, Sanderson et al. U.S. Pat. No. 4,922,036, Sanderson et al. U.S. Pat. No. 4,992,602, and Sanderson et al. U.S. Pat. No. 5,025,113.

It is known to use tertiary butyl hydroperoxide prepared by the oxidation of isobutane as a feedstock, together with propylene for epoxidation reaction process wherein the propylene and tertiary butyl hydroperoxide are converted to propylene oxide and tertiary butyl alcohol as shown, for example, by Marquis et al. U.S. Pat. No. 5,093,506 and Marquis et al. U.S. Pat. No. 5,151,530.

It is known to use tertiary butyl alcohol obtained by the oxidation of isobutane as a feedstock, together with methanol as a feedstock, for an etherification reaction process wherein the tertiary butyl alcohol and methanol are reacted to form methyl tertiary butyl ether.

SUMMARY OF THE INVENTION

In accordance with the present invention, tertiary butyl alcohol is prepared from isobutane by noncatalytically reacting isobutane with oxygen to provide an initial liquid reaction product comprising isobutane, peroxides including tertiary butyl hydroperoxide, and impurities; the initial liquid reaction product is deisobutanized and charged to a first decomposition zone together with a soluble peroxide decomposition catalyst, the first decomposition reactor within this zone being fitted with a fractionating column and a condenser wherein the first decomposition reaction product is fractionated to provide a first liquid decomposition product comprising tertiary butyl alcohol, catalyst, hydroperoxides and contaminants and a first vaporized decomposition product comprising oxygen, tertiary butyl alcohol and contaminants; the first vaporized decomposition product being cooled to condense normally liquid components to provide a liquid reflux stream for the fractionating column and a tertiary butyl alcohol reaction product; the first liquid decomposition product being charged to a second decomposition zone to substantially completely decompose the peroxides in the first liquid decomposition product to form a second liquid decomposition product which is separated in a second distillation column into a third lighter overhead fraction comprising tertiary butyl alcohol and a third heavier liquid fraction comprising liquid reaction products including tertiary butyl alcohol and residual quantities of hydroperoxide contaminants and soluble decomposition catalyst which are recycled to the first decomposition reactor.

More particularly, this invention relates to a process for producing tertiary butyl alcohol from isobutane which comprises the steps of:

noncatalytically contacting isobutane with oxygen in a first reactor under oxidation reaction conditions selected to provide an initial reaction product comprising a major amount of unreacted isobutane, minor amounts of peroxide including tertiary butyl hydroperoxide, and tertiary butyl alcohol and contaminating quantities of oxygen-containing impurities including methanol, acetone and water;

separating the initial reaction product in the first distillation column into a first lighter distillation fraction comprising isobutane and a first heavier liquid distillation fraction comprising the remainder of said initial liquid reaction product;

charging the first heavier liquid distillation fraction and a catalytically effective amount of a soluble peroxide decomposition catalyst to a first decomposition zone wherein a first decomposition reactor fitted with a fractionating column and a condenser and establishing catalytic peroxide decomposition conditions of time, temperature and pressure therein correlated to provide a first liquid decomposition product comprising tertiary butyl alcohol, soluble decomposition catalyst, a reduced quantity of hydroperoxides and contaminating quantities of oxygen-containing impurities, including methanol, acetone and water, and a first vaporized decomposition product comprising oxygen, tertiary butyl alcohol and contaminating quantities of oxygen-containing impurities including methanol, acetone and water;

venting the first vaporized decomposition product through the fractionating column and condensing the normally liquid components thereof to form a first condensate including tertiary butyl alcohol and oxygen-containing impurities including methanol and acetone and water;

returning a portion of the first condensate to said fractionating column as reflux and recovering the remaining portion as a tertiary butyl alcohol reaction product;

charging the first liquid decomposition product to a second decomposition zone comprising one or more serially connected reaction vessels and establishing hydroperoxide decomposition reaction conditions of time, temperature and pressure therein sufficient to substantially completely decompose the peroxide in the first liquid decomposition product and to form a second liquid decomposition product comprising tertiary butyl alcohol, minor quantities of peroxides, oxygenated impurities including methanol, acetone, oxygen, and water;

charging the second liquid decomposition product to a second distillation column and separating it therein into a third lighter overhead fraction comprising oxygen, and vaporized normally liquid components including tertiary butyl alcohol, water and oxygenated impurities including acetone and methanol, and a third heavier liquid fraction comprising normally liquid reaction by-products including tertiary butyl alcohol and residual quantities of hydroperoxide contaminants and liquid peroxide decomposition catalyst;

recycling at least a portion of the third heavier fraction to the first decomposition reactor;

condensing the normally liquid components of the third lighter overhead fraction to form a third condensate including tertiary butyl alcohol and oxygen-containing impurities including methanol, acetone and water, and returning a portion of the third condensate to the second distillation column as reflux and recovering the remaining portion as a tertiary butyl alcohol reaction product.

In accordance with one preferred embodiment of the present invention, a process is provided for continuously producing tertiary butyl alcohol from isobutane which comprises the steps of:

continuously noncatalytically contacting isobutane with oxygen in a first oxidation reaction zone under reaction conditions selected to provide an initial liquid reaction product comprising unreacted isobutane, peroxides including tertiary butyl hydroperoxide, tertiary butyl alcohol and contaminating quantities of oxygen-containing impurities including methanol, acetone and water;

continuously fractionating the initial reaction product in a first distillation column into a first lighter distillation fraction comprising isobutane and a first heavier liquid distillation fraction comprising the remainder of the initial liquid reaction product;

continuously charging the first heavier liquid distillation fraction and a catalytically effective amount of a liquid soluble molybdenum peroxide decomposition catalyst to a first decomposition zone containing a series of decomposition reactors, each of the reactors of the series being fitted with a fractionating column and a condenser and establishing catalytic peroxide decomposition reaction conditions in each of the vessels to provide a liquid reaction product comprising tertiary butyl alcohol, soluble peroxide decomposition catalyst, a reduced quantity of hydroperoxides and contaminating quantities of oxygen-containing impurities, including methanol, acetone and water, and a vaporized reaction product comprising oxygen, and vaporized normally liquid components including tertiary butyl alcohol and oxygen-containing impurities including methanol, acetone and water;

the reaction product of the first decomposition reactor of the series being continuously charged to the next succeeding reactor, the reaction product of the last of the series being continuously discharged from the first decomposition zone;

continuously venting vaporized reaction product from each of the vessels through a fractionating column associated therewith;

continuously condensing normally liquid components of each of the vented vaporized reaction products to form a condensate including tertiary butyl alcohol and oxygen containing impurities to form a condensate including tertiary butyl alcohol and oxygen-containing impurities comprising methanol, acetone and water;

continuously returning a portion of each of the condensates to the associated fractionating column as reflux and recovering the remaining portion as a tertiary butyl alcohol reaction product;

continuously charging the last of the series of liquid reaction products to a second decomposition zone and establishing hydroperoxide decomposition reaction conditions therein sufficient to substantially completely decompose the peroxides in said first liquid decomposition product and to form a second liquid decomposition product comprising tertiary butyl alcohol, minor quantities of peroxides, oxygenated impurities including methanol, acetone, and water;

continuously charging the second liquid decomposition product to a second distillation zone and separating it therein into a third lighter overhead fraction comprising oxygen and vaporized normally liquid components including tertiary butyl alcohol, water and oxygenated impurities and a third heavier liquid fraction comprising tertiary butyl alcohol, soluble decomposition catalyst, minor quantities of hydroperoxides and contaminating quantities of oxygen-containing impurities including methanol, acetone and water;

continuously recycling at least a portion of said third liquid fraction to said first decomposition reactor;

continuously condensing normally liquid components of said third lighter overhead fraction to form a third condensate including tertiary butyl alcohol and oxygenated impurities;

continuously returning a portion of the third condensate to said second distillation column as reflux and recovering the remaining portion of the tertiary butyl alcohol as a reaction product;

continuously charging at least a portion of the tertiary butyl alcohol reaction product and methanol to a methyl tertiary butyl reaction zone and converting it therein into methyl tertiary butyl ether;

continuously charging a portion of the first heavier liquid distillation product and propylene to an epoxidation zone under conversion conditions selected to convert the propylene and tertiary butyl hydroperoxide to propylene oxide and tertiary butyl alcohol; and returning at least a portion of the tertiary butyl alcohol product formed in the epoxidation zone to the methyl tertiary butyl ether reaction zone.

DESCRIPTION OF THE PROCESS OF THE PRESENT INVENTION

Feedstocks

The feedstocks to be used in accordance with the present invention are isobutane and oxygen. The isobutane may be used in purified form or as a component of a butane fraction containing other butanes such as normal butane. The oxygen may be used as concentrated molecular oxygen or as air, in which case nitrogen will be present as a diluent.

The Catalytic Decomposition of Tertiary Butyl Hydroperoxide

In accordance with the present invention, the initial reaction is conducted on a noncatalytic basis for a number of reasons. An enhanced amount of tertiary butyl hydroperoxide is formed which can be used for use in the manufacture of propylene oxide whereas if a catalyst is used the production of tertiary butyl hydroperoxide is limited. Also, if a catalyst is present, the tertiary butyl hydroperoxide will be contaminated with a trace quantity of soluble metals which are deleterious in a propylene epoxidation process.

In accordance with the present invention, the initial reaction product is fractionated in the first distillation column to separate a lighter distillation fraction comprising isobutane which is suitably recycled to the first oxidation reactor and a first heavier liquid fraction comprising the remainder of the initial liquid reaction product. All or a portion of the initial liquid reaction product is brought into contact with the hydroperoxide decomposition catalyst in a first decomposition reactor in order to substantially decompose the tertiary butyl hydroperoxide to form tertiary butyl alcohol with oxygen and oxygen-containing impurities as the byproduct.

It is known to prepare tertiary butyl alcohol by the catalytic decomposition of tertiary butyl hydroperoxide. Thus, Grane et al. disclose one such process in U.S. Pat. No. 4,294,999 wherein a soluble molybdenum catalyst is used.

Other catalysts useful for the catalytic conversion of tertiary butyl hydroperoxide to tertiary butyl alcohol are disclosed by Sanderson et al. in a series of U.S. patents. Thus, in U.S. Pat. No. 4,912,267 it is disclosed that a suitable catalyst is a base-promoted metal phthalocyanine catalyst such as a phthalocyanine of a metal of Group IB, Group VIIB or Group VIIIB of the Periodic Table (e.g., chloroferric phthalocyanine). A soluble ruthenium catalyst promoted with a bidentate ligand may also be used, as disclosed in U.S. Pat. No. 4,922,033. Also, Sanderson et al. disclose the use of metal porphine catalysts optionally promoted with alkyl thiols and amines such as iron (III) or manganese (III) porphine in U.S. Pat. No. 4,922,034. The catalyst used to prepare tertiary butyl alcohol by the decomposition of tertiary butyl hydroperoxide in the process of Sanderson et al. U.S. Pat. No. 4,922,035 is a metal phthalocyanine catalyst promoted with a $C_1$ to $C_{18}$ thiol and a free radical inhibitor (e.g., chloroferric phthalocyanine dodecane thiol or 2,3-dihydroxynaphthalene). Borate promoted catalysts are disclosed as useful for the production of tertiary butyl alcohol by the catalytic decomposition of tertiary butyl hydroperoxide in Sanderson et al. U.S. Pat. No. 4,922,036. The process of Sanderson et al. U.S. Pat. No. 4,910,349 discloses the preparation of tertiary butyl alcohol from tertiary butyl hydroperoxide using a metal phthalocyanine catalyst promoted with a rhenium compound (e.g., chloroferric phthalocyanine and rhenium heptoxide-p-dioxane or oxytrichloro-bis-(triphenylphosphine) rhenium V). The use of soluble iron compounds and soluble ruthenium compounds as catalysts in the preparation of tertiary butyl alcohol from tertiary butyl hydroperoxide is disclosed in Sanderson et al. U.S. Pat. No. 5,025,113.

The preferred catalysts are soluble molybdenum and iron compounds.

In accordance with the present invention, the decomposition reactors in the first decomposition zone are fitted with a fractionating column and a condenser and reaction conditions of time, temperature and pressure are utilized, including a temperature of about 50° to 200° C., a pressure of about 5 to about 50 psia, and a reaction time of about 0.25 to about 4 hours, and more preferably a reaction temperature of about 80° to 120° C., a reaction pressure of about 10 to 25 psia, and a reaction time of about 0.5 to 1.0 hours, such that the reaction product comprises both a liquid phase and a vapor phase.

When the reaction is conducted in the manner just described, the vapor phase will comprise normally gaseous components such as oxygen, and vaporized normally liquid components including tertiary butyl alcohol and oxygen-containing impurities such as acetone, methanol and water.

In accordance with the present invention, the vapor phase is vented from the reactor through the fractionating column and cooled in a condenser to an extent sufficient to liquify the vaporized normally liquid components and to form a first condensate comprising tertiary butyl alcohol and oxygen-containing impurities including methanol, acetone and water. A portion of the condensate is returned to the fractionating column as reflux and the remainder is recovered as tertiary butyl alcohol reaction product. The liquid decomposition product formed in the first decomposition reactor will also comprise tertiary butyl alcohol, but will contain a minor amount (e.g., up to 25 wt. %) of unreacted tertiary butyl hydroperoxide and other peroxide contaminants as well as heavier reaction byproducts such as carboxylic acids.

The Noncatalytic Oxidation of Isobutane

In accordance with the present invention, the isobutane and oxygen are reacted in liquid phase noncatalytically in order to provide a reaction product comprising unreacted isobutane, tertiary butyl hydroperoxide, tertiary butyl alcohol, and contaminants including other peroxides such as ditertiary butyl peroxide, etc., and oxygenated impurities including methanol, acetone and water.

The process is a known process being described, for example, in Winkler et al. U.S. Pat. No. 2,845,461 wherein appropriate reaction conditions are recited such as a temperature of about 100° to about 150° C., and a pressure of about 400 psig to 1000 psig. A preferred pressure range is within the range of about 500 to about 750 psig. Reaction times may suitably be within the range of about 1 to about 8 hours, and more preferably from about 4 to about 6 hours.

Under reaction conditions as described above, the effluent from the first oxidation reactor will typically comprise from about 60 to about 70 wt. % of unreacted isobutane, about 15 to about 20 wt. % of tertiary butyl hydroperoxide, about 10 to about 15 wt. % of tertiary butyl alcohol, and minor quantities of water, methanol, acetone, and other oxygenated impurities.

Removal of Peroxide Contaminants From Liquid Tertiary Butyl Alcohol

Although a high level of conversion of tertiary butyl hydroperoxide to tertiary butyl alcohol can be obtained when the first decomposition reaction is conducted in the described manner, nevertheless, the conversion will normally amount to only about 5 to about 50 wt. %. As a consequence, the liquid reaction product formed in the oxidation reactor will comprise not only tertiary butyl alcohol, but also up to about 25 wt. % of tertiary butyl hydroperoxide and other peroxide contaminants and about 0 to about 2 wt. % of other contaminants such as acetone, methanol and water.

In accordance with the present invention, the first decomposition product is charged to a second decomposition zone under reaction conditions of time, temperature and pressure sufficient to substantially completely decompose the peroxides and to form a second decomposition product comprising tertiary butyl alcohol, minor quantities of peroxides and oxygenated impurities including methanol, acetone, oxygen, nitrogen and water.

It is known to purify tertiary butyl alcohol containing up to about 5 wt. % of peroxide contaminants. The peroxide contaminants are substantially completely decomposed in the second decomposition zone. The final product will normally contain from about 0 to about 1 wt. % of peroxides.

The reaction conditions to be utilized in the second decomposition zone will suitably include a temperature of about 80° to about 170° C., and more preferably from about 100° to about 140° C., a pressure of about 40 to about 150 psig, and more preferably from about 70 to about 80 psig, and a reaction time of about 0.25 to about 6 hours, and more preferably from about 0.5 to about 2 hours.

The second decomposition product which will comprise tertiary butyl alcohol, from about 0 to about 1 wt. % of peroxide impurities, and from about 0 to about 10 wt. % of oxygen-containing impurities including methanol, acetone and water, as well as normally gaseous byproducts such as oxygen, is withdrawn from the second decomposition zone and charged to a second distillation column wherein it is separated into a third lighter overhead fraction comprising oxygen and vaporized normally liquid components including tertiary butyl alcohol, water and oxygenated impurities including acetone and methanol which are passed through a condenser in order to condense (i.e., liquify) the normally liquid components. A portion of the second condensate is returned to the second distillation column as reflux and the remaining portion is recovered as a tertiary butyl alcohol product.

A heavier fraction is withdrawn from the second distillation column comprising tertiary butyl alcohol, residual peroxide contaminants, solubilized catalyst, and heavier byproducts such as carboxylic acids. The third heavier liquid fraction is recycled to the first decomposition zone in accordance with the preferred embodiment of the present invention.

As indicated previously, all or a portion of the tertiary butyl alcohol reaction products may be used as feedstocks for the manufacture of methyl tertiary butyl ether. When this is to be done, tertiary butyl alcohol is charged, together with methanol, to an appropriate methyl tertiary butyl preparation unit where they are reacted in the presence of an appropriate catalyst to provide methyl tertiary butyl ether. A representative process of this nature is disclosed, for example, in Kruse et al. U.S. Pat. No. 5,243,091.

As indicated, a portion of the first heavier liquid distillation fraction comprising debutanized initial reaction product may be utilized as a feedstock for the preparation of propylene oxide and additional tertiary butyl alcohol. When this is to be done, a portion of the first heavier liquid distillation fraction and propylene are charged to an epoxidation reaction unit where they are catalytically reacted in the presence of a soluble molybdenum catalyst to provide propylene oxide and additional tertiary butyl alcohol. A representative process of this nature is disclosed, for example, in Marquis et al. U.S. Pat. Nos. 5,093,506 and 5,151,530.

BRIEF DESCRIPTION OF THE DRAWINGS

In the drawings:

Turning now to FIG. 1, there is schematically shown an oxidation reactor 10 to which oxygen is charged by a line 12 and to which isobutane is charged by a line 14.

Figure 1:
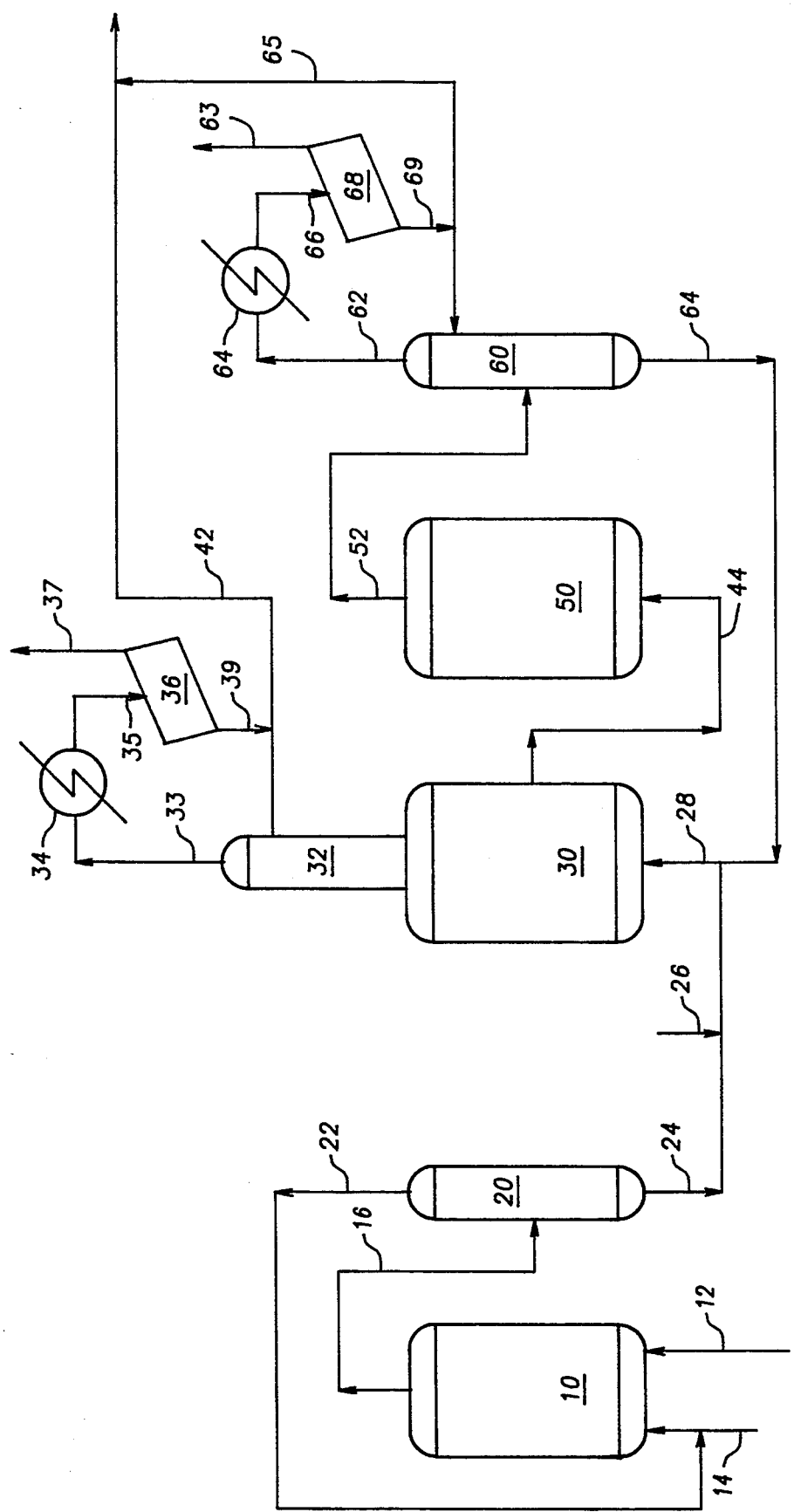
FIG. 1 is a schematic flow sheet illustrating a preferred method for the practice of the present invention wherein only one decomposition reactor and associated fractionating column are used.

Noncatalytic oxidation reaction conditions are established in the oxidation reactor 10 correlated to provide an initial reaction product comprising unreacted butane, peroxide reaction products including tertiary butyl hydroperoxide, ditertiary butyl peroxide, etc., tertiary butyl alcohol, oxygenated impurities including methanol and acetone, water, nitrogen, and oxygen. Suitably, the noncatalytic reaction conditions used in the oxidation reactor 10 will include a temperature of about 100° to about 150° C., a pressure of at least about 400 psig, and a reaction time of about 1 to about 8 hours. An initial reaction product having the described composition is continuously withdrawn from the oxidation reactor 10 by way of a discharge line 16 leading to a first distillation column 20 wherein the initial reaction product is fractionated under conditions selected to provide for a first lighter fraction 22 consisting essentially of isobutane and a first heavier fraction comprising the remainder of the initial liquid reaction product which is discharged by way of a line 24. All or a portion of the isobutane in the line 22 may be recycled to the isobutane charge line 14 for the oxidation reactor 10.

An appropriate liquid hydroperoxide decomposition catalyst such as a soluble molybdenum catalyst is added to the first heavier liquid distillation fraction in the line 24 by way of a line 26 leading to a charge line 28 for a first decomposition reactor 30.

The first decomposition oxidation reactor 30 is fitted with a fractionating column 32 provided with a condenser 34 and a condensate drum 36.

Within the first decomposition reactor 30, reaction conditions are correlated so as to provide both a first liquid decomposition product and a first vaporized decomposition product. The first vaporized decomposition product will suitably comprise normally gaseous components including oxygen and vaporized normally liquid components including tertiary butyl alcohol and oxygen-containing impurities such as methanol, acetone and water. The first liquid decomposition product will comprise tertiary butyl alcohol, unreacted tertiary butyl hydroperoxide, soluble catalyst, heavier reaction byproducts, etc. The first vaporized decomposition product is discharged from the fractionating column 32 by a line 33 leading to condenser 34 wherein the vaporized normally liquid components are condensed. The effluent from the condenser 34 is charged by a line 35 to a decanter 36 wherein the normally gaseous components such as oxygen are separated from the liquid condensate for discharge by way of a line 37. The liquid condensate is discharged from the condensate drum 36 by a line 39. A portion of the condensate in the line 39 is returned to the fractionating column 32 by way of a line 40 as reflux and the remaining portion of the condensate is recovered by way of line 42 as a tertiary butyl alcohol reaction product.

The first liquid decomposition product is discharged from the first decomposition reactor 30 by way of a line 44 leading to a second decomposition reactor 50.

Within the second decomposition reactor 50, reaction conditions of time, temperature and pressure therein sufficient to substantially decompose the peroxides in the first liquid decomposition product and to form a second liquid decomposition product comprising tertiary butyl alcohol, minor quantities of peroxide impurities, oxygen-containing impurities including methanol, acetone and water, and minor quantities of oxygen. Suitably, the reaction conditions within the second decomposition reactor 50 will comprise a temperature of about 80° to about 170° C., and more preferably from about 100° to about 140° C., a pressure of about 40 to about 150 psig and more preferably from about 70 to about 80 psig, and a reaction time of about 0.25 to about 6 hours and more preferably from about 0.5 to about 2 hours. The second decomposition product is discharged from the second decomposition reactor 50 by a line 52 leading to a second distillation column 60 wherein it is separated into a third lighter overhead fraction 62 comprising oxygen, and vaporized normally liquid components including tertiary butyl alcohol, water and oxygenated impurities including acetone and methanol, and a third heavier fraction 64 comprising normally liquid byproducts including tertiary butyl alcohol, residual quantities of peroxide contaminants, and dissolved liquid peroxide decomposition catalyst.

The third heavier fraction 64 is continuously recycled to the charge line 28 for the second decomposition reactor 30.

The third lighter overhead fraction 62 is passed to a condenser 64 wherein the vaporized normally liquid components are condensed to form a third condensate which is charged by way of a line 66 to a condensate drum 68. The third condensate is discharged from the condensate drum 68 by a line 69, and a portion of the condensate in the line 69 is returned to the second distillation column 60 as reflux by a line 67 while the remaining portion is discharged from the system by a line 65 as a tertiary butyl alcohol product.

The normally gaseous components of the third lighter overhead fraction 62, are removed from the condensate drum 68 by way of a line 63.

Figure 2:
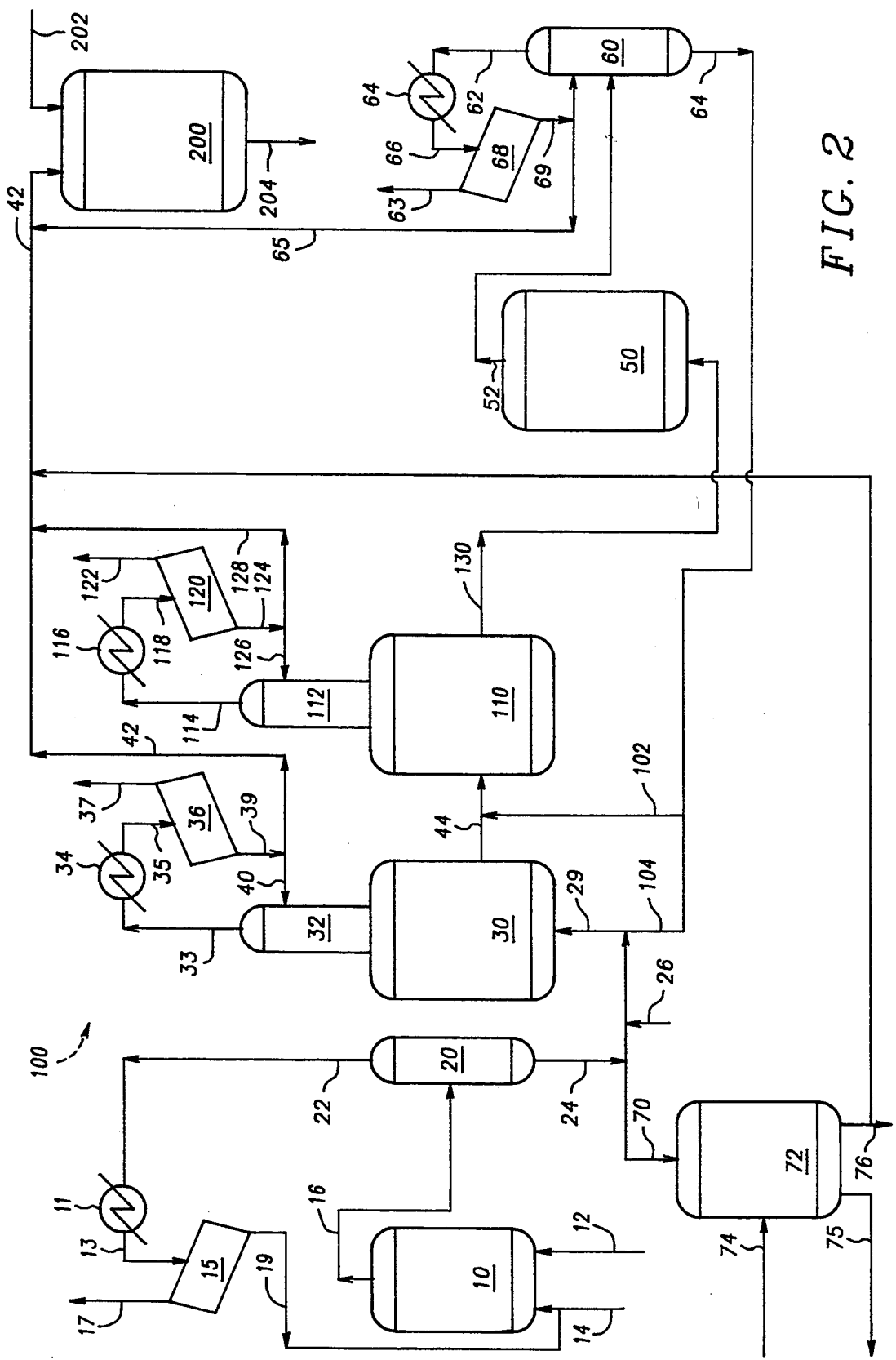
FIG. 2 is a schematic flow sheet illustrating a modified embodiment of the present invention wherein a plurality of decomposition reactors fitted with fractionating columns are utilized, wherein a portion of the initial oxidation reaction product is used as a feedstock for a propylene epoxidation reaction and wherein the tertiary butyl alcohol is utilized as a feedstock to be charged to a methyl tertiary butyl ether reaction zone.

Turning now to FIG. 2, a modified form of the present invention is shown wherein a first decomposition zone is provided comprising a plurality of decomposition reaction vessels.

In accordance with this embodiment of the present invention, and as described above, an oxidation reactor 10 is provided to which oxygen is charged by way of a line 12 and to which isobutane is charged by way of a line 14. The oxygen and isobutane are noncatalytically reacted in the oxidation reactor 10 in the manner described above to provide an initial reaction product 16 comprising unreacted isobutane, peroxides including tertiary butyl hydroperoxide, tertiary butyl alcohol and contaminating quantities of oxygen-containing impurities including methanol, acetone and water. The initial reaction product 16 is charged to a first distillation column 20 where it is separated into a first lighter distillate fraction 22 comprising isobutane, oxygen, etc., and a first heavier liquid fraction 24.

The first overhead distillate fraction 22 is charged to a condenser 11 wherein the isobutane and other vaporized normally liquid components are condensed to form a primary condensate which is discharged through the condenser 11 by a line 13 leading to a primary condensate drum 15. Oxygen and other noncondensible gasses are vented from the primary drum 15 by a line 17 and the remainder of the primary condensate is discharged from the drum 15 by a line 19 for recycle to the oxidation reactor 10 by way of isobutane charge line 14.

In accordance with the present invention, a portion of the first heavier distillate fraction 24 is charged by way of a line 70 to an epoxidation reaction zone 72. Propylene is also charged to the epoxidation reaction zone 72 by a line 74. Within the epoxidation reaction zone 72 propylene and tertiary butyl hydroperoxide contained in the first heavier liquid distillation fraction 70 react in the presence of a soluble molybdenum catalyst to form propylene oxide and additional tertiary butyl alcohol. The epoxidation reaction zone may be constructed and operated in the manner disclosed and described in Marquis et al. U.S. Pat. No. 5,151,530.

Product propylene oxide is discharged from the epoxidation reaction zone 72 by a line 75 and product tertiary butyl alcohol is discharged from the epoxidation reaction zone 72 by a line 76.

The remaining portion of the first heavier liquid distillation fraction 24 is charged by a line 29 to a first decomposition zone designated generally by the numeral 100.

A catalytically effective amount of a suitable tertiary butyl hydroperoxide decomposition catalyst (e.g., from about 5 to about 1000 ppm of a soluble molybdenum catalyst) is charged by line 26 and mixed with the remaining portion of the first heavier liquid distillation fraction 24 and the mixture is charged by way of a charge line 29 to the first of a plurality of reaction vessels (e.g., 2), such as reaction vessels 30 and 110.

AS described above in connection with FIG. 1, the decomposition vessel 30 is operated so as to provide a liquid reaction product and a vaporized reaction product. The vaporized reaction product is discharged from the decomposition vessel 30 through a fractionating column 32 by way of a vent line 33 leading to a condenser 34 wherein the normally liquid components of the fraction 33 are condensed to provide a condensate which is discharged by a line 35 leading to a condensate drum 36. Noncondensible gases such as oxygen are discharged from the condensate drum 36 by a line 37 and the liquid condensate is discharged from drum 36 by a line 39. A portion of the condensate in the line 39 is returned to the fractionating column 32 by a line 40 as reflux and the remaining portion is discharged by a line 42 as tertiary butyl alcohol reaction product.

The liquid decomposition product 44 is charged to the next hydroperoxide decomposition reaction vessel 110, which is operated in the same manner as peroxide decomposition reactor 30.

The vaporized reaction product from the second hydroperoxide decomposition vessel 100 comprises vaporized normally liquid components including tertiary butyl alcohol and oxygen-containing impurities such as methanol, acetone and water and noncondensible gasses such as oxygen and is discharged from associated fractionating column 112 by a line 114 leading to a condenser 116 wherein the normally liquid components are condensed to provide a condensate which is discharged by a line 118 leading to a condensate drum 120. Noncondensible gasses are discharged from the condensate drum 120 by a line 122 and condensate is discharged from the condensate drum by a line 124. A portion of the condensate 124 is returned to the fractionating column 112 by a line 126 as reflux and the remaining portion of the condensate 124 is discharged by a line 128 leading to the tertiary butyl alcohol product line 42.

Although only two hydroperoxide decomposition vessels, namely reactors 30 and 110, are shown in FIG. 2, it will be understood that additional hydroperoxide decomposition vessels operated in the described manner can be connected in series, if desired.

In accordance with the present invention, the last of the series of liquid hydroperoxide decomposition products is discharged from the last of the series of hydroperoxide reaction vessels (e.g., hydroperoxide decomposition vessel 110) by a line 130 leading to a second hydroperoxide decomposition zone. Within this second decomposition zone is reactor 50 which is constructed and operated in the manner described above in respect of FIG. 1. Although only one decomposition reactor, namely reactor 50, is shown in FIG. 2, it will be understood that additional hydroperoxide decomposition vessels operated in the described manner can be connected in series, if desired. The second hydroperoxide decomposition product is discharged from the second decomposition reactor 50 by a line 52 leading to a second distillation column 60 wherein an overhead fraction is taken comprising tertiary butyl alcohol and other lighter normally liquid reaction components and noncondensible gases such as oxygen.

The third lighter overhead fraction 62 from the second distillation column 60 is charged to a condenser 64 wherein the normally liquid components are condensed to provide a condensate 66 which is charged to a condensate drum 68. Noncondensible gasses such as oxygen are discharged from the condensate drum 68 by a line 63 and the condensate is discharged to the condensate drum 68 by a line 69. A portion of the condensate in the line 69 is returned to the second distillation column 60 as reflux by a line 67 and the remaining portion is discharged by way of a line 65 leading to the tertiary butyl alcohol product line 42.

The third heavier fraction 61 discharged from the second distillation column 60 is recycled in part by way of line 102 to second decomposition vessel 110 and, in part, by the line 104 to first decomposition vessel 30.

In accordance this embodiment of the present invention, tertiary butyl alcohol in the product line 42 is charged to a methyl tertiary butyl ether reaction zone 200 which is constructed and operated, for example, in the manner disclosed and described in Kruse et al. U.S. Pat. No. 5,243,091. In accordance with this embodiment, methanol is charged to the methyl tertiary butyl ether reaction zone 200 by a line 202 and product methyl tertiary butyl ether is discharged from the methyl tertiary butyl ether reaction zone 200 by a line 204.

Having thus described our invention, what is claimed is:

1. A process for producing tertiary butyl alcohol from isobutane which comprises the steps of:

noncatalytically contacting isobutane with oxygen in an oxidation reactor under oxidation reaction conditions selected to provide an initial liquid reaction product comprising unreacted isobutane, peroxides including tertiary butyl hydroperoxide and tertiary butyl alcohol and contaminating quantities of oxygen-containing impurities including methanol, acetone and water, distilling said initial reaction product in a first distillation column into a first lighter distillation overhead fraction comprising isobutane and a first heavier liquid distillation fraction comprising the remainder of said initial liquid reaction product, charging said first heavier liquid distillation fraction and a catalytically effective amount of a soluble peroxide decomposition catalyst to a first hydroperoxide decomposition reactor fitted with a fractionating column and a condenser and establishing catalytic peroxide decomposition conditions of time, temperature and pressure therein correlated to provide as a second heavier liquid fraction a first liquid hydroperoxide decomposition product comprising tertiary butyl alcohol, peroxide decomposition catalyst, a reduced quantity of peroxides, and contaminating quantities of oxygen-containing impurities including methanol, acetone and water, and as a second lighter overhead fraction a first vaporized hydroperoxide decomposition product comprising oxygen and vaporized normally liquid components comprising tertiary butyl alcohol and contaminating quantities of oxygen-containing impurities including methanol, acetone and water, discharging said first vaporized decomposition product through said fractionating column, condensing normally liquid components of said first vaporized decomposition product to form a first condensate including tertiary butyl alcohol and oxygen-containing impurities including methanol, acetone and water, returning a portion of said first condensate to said fractionating column as reflux and recovering the remaining portion as a tertiary butyl alcohol reaction product, charging said first liquid decomposition product to a second hydroperoxide decomposition reactor and establishing hydroperoxide decomposition reaction conditions of time, temperature and pressure therein sufficient to substantially completely decompose the peroxides in said first liquid decomposition product and to form a second hydroperoxide decomposition product comprising tertiary butyl alcohol, minor quantities of peroxides, oxygen-containing impurities including methanol, acetone and water and oxygen, charging said second decomposition product to a second distillation column and separating it therein into a third lighter overhead fraction comprising oxygen, and vaporized normally liquid components including tertiary butyl alcohol, water and oxygen-containing impurities including acetone and methanol and a third heavier liquid fraction comprising normally liquid reaction by-products, including tertiary butyl alcohol and residual quantities of hydroperoxide contaminants and dissolved peroxide decomposition catalyst, recycling said third heavier fraction to said first hydroperoxide decomposition oxidation reactor, condensing normally liquid components of said third lighter overhead fraction to form a second condensate including tertiary butyl alcohol and oxygen-containing impurities including methanol, acetone and water, returning a portion of said second condensate to said second distillation column as reflux and recovering the remaining portion as a tertiary butyl alcohol reaction product.

2. A process as in claim 1 wherein the soluble heterogeneous peroxide decomposition catalyst is a tertiary butyl alcohol soluble organic compound of molybdenum, chromium, cobalt, nickel, iron or manganese and mixtures thereof.

3. A process for continuously producing tertiary butyl alcohol from isobutane which comprises the steps of:

continuously noncatalytically contacting isobutane with oxygen in an oxidation reactor under oxidation reaction conditions including a temperature of about 100° to about 150° C., a pressure of about 500 to about 1,000 psig and a reaction time of about 1 to about 8 hours selected to provide an initial liquid reaction product comprising unreacted isobutane, peroxides, including tertiary butyl hydroperoxide, tertiary butyl alcohol and contaminating quantities of oxygen-containing impurities including methanol, acetone and water, continuously separating said initial reaction product in a first distillation column into a first lighter distillation fraction comprising isobutane and a first heavier liquid distillation fraction comprising the remainder of said initial liquid reaction product, continuously charging said first heavier liquid distillation fraction and a catalytically effective amount of a liquid, soluble molybdenum peroxide decomposition catalyst to a first hydroperoxide decomposition reactor fitted with a fractionating column and a condenser and establishing catalytic peroxide decomposition conditions including a temperature of about 50° to about 200° C., a pressure of about 5 to about 50 psia and a reaction time of about 0.25 to about 4 hours correlated to provide as a second heavier fraction a hydroperoxide decomposition product comprising a first liquid hydroperoxide decomposition reaction product comprising tertiary butyl alcohol, decomposition catalyst, a reduced quantity of hydroperoxides, and contaminating quantities of oxygen-containing impurities including methanol, acetone and water, and as a second lighter overhead fraction a first vaporized decomposition product comprising oxygen, and vaporized normally liquid components comprising tertiary butyl alcohol and contaminating quantities of oxygen-containing impurities including methanol, acetone and water, continuously condensing normally liquid components of said first vaporized decomposition product to form a first condensate including tertiary butyl alcohol and oxygen-containing impurities including methanol and acetone and water, continuously returning a portion of said first condensate to said fractionating column as reflux and recovering the remaining portion as a tertiary butyl alcohol reaction product, continuously charging said first liquid decomposition product to a second decomposition reactor and establishing hydroperoxide decomposition reaction conditions therein including a temperature of about 80° to about 170° C., a pressure of about 40 to about 150 psig and a reaction time of about 0.25 to about 6 hours sufficient to substantially completely decompose the peroxides in said first liquid decomposition product and to form a second decomposition product comprising tertiary butyl alcohol, minor quantities of peroxides, oxygen-containing impurities including methanol, acetone and water and oxygen, continuously charging said second decomposition product to a second distillation zone and separating it therein into a third lighter overhead fraction comprising oxygen and vaporized normally liquid components including tertiary butyl alcohol, water and oxygen-containing impurities including acetone and methanol and a third heavier liquid fraction comprising normally liquid reaction by-products, including tertiary butyl alcohol and residual quantities of peroxide contaminants and liquid peroxide decomposition catalyst, continuously recycling said third heavier fraction to said first hydroperoxide decomposition reactor, continuously condensing normally liquid components of said third lighter overhead fraction to form a second condensate including tertiary butyl alcohol and oxygen-containing impurities including methanol, acetone and water, continuously returning a portion of said second condensate to said second distillation column as reflux and recovering the remaining portion as a tertiary butyl alcohol reaction product.

4. A process for continuously producing tertiary butyl alcohol from isobutane which comprises the steps of:

continuously noncatalytically contacting isobutane with oxygen in a first oxidation reactor under oxidation reaction conditions including a temperature of about 80° to about 120° C. a pressure of about 10 to about 25 psig and a reaction time of about 0.5 to about 1 hour selected to provide an initial liquid reaction product comprising unreacted isobutane, peroxides, including tertiary butyl hydroperoxide, tertiary butyl alcohol and contaminating quantities of oxygen-containing impurities including methanol, acetone and water, continuously distilling said initial reaction product in a first distillation column into a first lighter distillation overhead fraction comprising isobutane and a first heavier liquid distillation fraction comprising the remainder of said initial liquid reaction product, continuously charging at least a portion of said first heavier liquid distillation fraction and a catalytically effective amount of a soluble molybdenum hydroperoxide decomposition catalyst to a first hydroperoxide decomposition zone containing a plurality of hydroperoxide reaction vessels, each hydroperoxide reaction vessel being fitted with a fractionating column and a condenser, said first heavier liquid distillation fraction being charged to the first of the series of hydroperoxide reaction vessels in the first hydroperoxide decomposition zone and the peroxide decomposition product from the first and succeeding hydroperoxide decomposition vessels in the series being continuously charged to the next succeeding decomposition vessel, the last of the series of hydroperoxide decomposition products being discharged from the first hydroperoxide decomposition zone, establishing catalytic hydroperoxide decomposition reaction conditions in said peroxide decomposition vessels including a temperature of about 50° to about 200° C., a pressure of about 5 to 50 psia and a reaction time of about 0.25 to about 4 hours correlated to provide as a second heavier liquid fraction a liquid hydroperoxide decomposition reaction product in each of the hydroperoxide reaction vessels comprising tertiary butyl alcohol, soluble molybdenum hydroperoxide decomposition catalyst, a reduced quantity of hydroperoxides and contaminating quantities of oxygen-containing impurities including methanol, acetone and water and as a second lighter overhead fraction a vaporized hydroperoxide decomposition product comprising oxygen, tertiary butyl alcohol and contaminating quantities of oxygen-containing impurities including methanol, acetone and water, continuously discharging the vaporized hydroperoxide decomposition product of each of the decomposition vessels through the fractionating column associated therewith, condensing normally liquid components of said vaporized hydroperoxide decomposition product to form a condensate including tertiary butyl alcohol and oxygen-containing impurities including methanol and acetone and water, continuously returning a portion of each of said condensates to its said associated fractionating column as reflux and recovering the remaining portion as a tertiary butyl alcohol reaction product, continuously charging said last of the series of liquid hydroperoxide decomposition products to a second hydroperoxide decomposition zone and establishing hydroperoxide decomposition reaction conditions including a temperature of about 80° to about 170° C., a pressure of about 40 to about 150 psig and a reaction time of about 0.25 to about 6 hours sufficient to substantially completely decompose the hydroperoxides in said second liquid hydroperoxide decomposition product and to form a second hydroperoxide decomposition product comprising tertiary butyl alcohol, minor quantities of peroxides, oxygen-containing impurities including methanol, acetone and water and oxygen, continuously charging said second hydroperoxide decomposition product to a second distillation zone and separating it therein into a third lighter overhead fraction comprising oxygen and vaporized normally liquid components including tertiary butyl alcohol, water and oxygen-containing impurities including acetone and methanol and a third heavier liquid fraction comprising normally liquid reaction products, including tertiary butyl alcohol and residual quantities of hydroperoxide contaminants and dissolved hydroperoxide decomposition catalyst, continuously recycling said third heavier fraction to said first hydroperoxide decomposition zone, continuously condensing normally liquid components of said third lighter overhead fraction to form a second condensate including tertiary butyl alcohol and oxygen-containing impurities including methanol and acetone and water, continuously returning a portion of said second condensate to said second distillation column as reflux and recovering the remaining portion as a tertiary butyl alcohol reaction product.

5. A process as in claim 4 wherein at least a portion of the said tertiary butyl alcohol reaction product is charged together with methanol to a methyl tertiary butyl ether reaction zone wherein the methanol and tertiary butyl alcohol are converted to methyl tertiary butyl ether.

6. A process as in claim 4 wherein a portion of the first heavier liquid distillation fraction and propylene are charged to an epoxidation conversion reactor together with a molybdenum epoxidation catalyst and converted therein into propylene oxide and a tertiary butyl alcohol product.

7. A process as in claim 6 wherein the tertiary butyl alcohol product is charged to a methyl tertiary butyl ether reaction zone.

* * * * *